(12) United States Patent
Nakatani (10) Patent No.: US 7,331,468 B2
(45) Date of Patent: Feb. 19, 2008

(54) DEVICE FOR SEPARATING FINE SOLID COMPONENTS, METHOD OF MANUFACTURING THE DEVICE, AND METHOD OF SEPARATING FINE SOLID COMPONENTS USING THE DEVICE

(75) Inventor: Masaya Nakatani, Takarazuka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 391 days.

(21) Appl. No.: 10/866,036

(22) Filed: Jun. 14, 2004

(65) Prior Publication Data
US 2004/0253691 A1 Dec. 16, 2004

(30) Foreign Application Priority Data
Jun. 13, 2003 (JP) .............................. 2003-169072

(51) Int. Cl.
*B07B 13/00* (2006.01)
*B07C 5/12* (2006.01)
(52) U.S. Cl. .................. 209/235; 209/680; 209/659
(58) Field of Classification Search ............... 209/660, 209/680, 659, 675, 676, 155; 347/27; 210/321.6, 210/348, 767; 422/101; 436/177
See application file for complete search history.

(56) References Cited

U.S. PATENT DOCUMENTS

| | | | |
|---|---|---|---|
| 5,705,070 A * | 1/1998 | Saaski et al. ............... 210/446 |
| 6,264,850 B1 * | 7/2001 | Silverbrook .................. 216/27 |
| 6,554,408 B1 * | 4/2003 | Miki et al. ...................... 347/70 |
| 6,811,752 B2 * | 11/2004 | Barbera-Guillem ......... 422/100 |
| 6,868,605 B2 * | 3/2005 | Maeng et al. ............... 29/890.1 |
| 6,926,386 B2 * | 8/2005 | Shin et al. ...................... 347/47 |
| 7,104,406 B2 * | 9/2006 | Chen et al. .................. 210/498 |
| 7,121,650 B2 * | 10/2006 | Chung et al. .................. 347/68 |
| 2002/0101486 A1 * | 8/2002 | Anagnostopoulos et al. .. 347/82 |
| 2004/0124173 A1 * | 7/2004 | Hess et al. ..................... 216/27 |
| 2004/0140732 A1 * | 7/2004 | Truninger et al. ........... 310/300 |

OTHER PUBLICATIONS

Sato et al., "A novel fabrication of in-channel 3-D micromesh structure using maskless multi-angle exposure and its microfilter application," *IEEE*, pp. 223-226 (2003).
Yoon et al., "Integrated vertical screen microfilter system using inclined SU-8 structures," *IEEE*, pp. 227-230 (2003).

* cited by examiner

*Primary Examiner*—Patrick Mackey
*Assistant Examiner*—Mark Hageman
(74) *Attorney, Agent, or Firm*—Steptoe & Johnson LLP (57) ABSTRACT

A device for separating a fine solid component includes a substrate and a diaphragm provided on the substrate. The substrate has a first surface and a second surface opposite the first surface. The substrate has a recess provided in the second surface, a cavity opening to the first surface, and a first through-hole allowing the recess to communicate with the cavity. The diaphragm has a second through-hole formed therein at a position corresponding to the cavity. The second through hole has a diameter smaller than a diameter of the first through-hole. This device and a method using the device enables only small solid components included in fluid having plural solid components having sizes different from each other to pass without clogging.

18 Claims, 9 Drawing Sheets

DEVICE FOR SEPARATING FINE SOLID COMPONENTS, METHOD OF MANUFACTURING THE DEVICE, AND METHOD OF SEPARATING FINE SOLID COMPONENTS USING THE DEVICE

FIELD OF THE INVENTION

The present invention relates to a device for separating fine solid components from solution including liquid component and the solid components, such as blood or emulsion, a method of manufacturing the device, and a method of separating fine solid components using the device.

BACKGROUND OF THE INVENTION

Fluid or powder fluid including plural kinds of solid components may be represented by river water, seawater, and blood. Each of these is mixture of liquid component and solid component. The component, such as sand, bacteria and blood cells, is precipitated or dispersed in solid form, and does not melt in the liquid component.

A method of separating such components, for example, for separating blood cells from blood will be described. Blood is usually collected as whole blood that includes blood plasma (liquid component), blood cells (solid component), and other components. However, only the blood cells or only blood plasma is often required for a blood test.

In order to inspect, for example, a blood-sugar level in blood, the amount of the blood sugar melting in the blood plasma is measured. In order to detect DNA, the DNA is extracted from leukocyte of blood cells. For this purpose, in a conventional method, in order to separate the collected whole blood into blood plasma and blood cells, the whole blood is put into a test tube, and then, a predetermined centrifugal force is applied to the blood with a centrifugal separator. This operation allows components of the whole blood in the test tube to receive different strength of centrifugal forces according to respective masses of the components, hence causing the components to be separated.

Then, the blood plasma is taken out by extracting supernatant liquid, and so the blood cells are taken from precipitation. Then, the separated component is measured in predetermined properties in a process of the test.

The conventional method employing the centrifugal separator has the following problem. The method requires a certain amount, e.g. several dozen milliliters, of whole blood in the test tube. Hence, it is difficult to separate solid components from liquid if the amount of sample is insufficient.

A method of separating solid components from a small amount of sample with a filter is disclosed in "A novel fabrication of In-channel 3-D micromesh structure using maskless multi-angle exposure and its microfilter application" (Hironobu Sato, MEMS2003, Kyoto, pp. 223-226, published by IEEE) and "Integrated vertical screen microfilter system using inclined SU-8 structure" (Yong-Kyu Yoon, MEMS2003, Kyoto, pp. 227-230, published by IEEE). In this method, a filter with porousness filtrates blood cells larger than a predetermined size to separate blood cells from a blood plasma. The size and the number of holes of the filter influences the characteristic of separation. Therefore, the filter needs to be optimally designed according to component to be separated. For example, a mesh-like filter with a desirable size can be manufactured by exposing photosensitive resist to light three-dimensionally, and the filter can have predetermined number and size of holes accurately.

In the conventional method employing a filter, the particle size of solid components varies according to a pressure for having fluid or powder fluid with plural components pass through the filter. Particularly, solid component particles having sizes different from each other can be hardly separated by this method. In order to take predetermined particles, a hole size of the filter is determined so that only particles smaller than the size pass through the filter. However, the predetermined particles are trapped by the filter, and clog the holes of the filter. Hence, the particles may prevent smaller particles from passing through the filter.

SUMMARY OF THE INVENTION

A device for separating a fine solid component includes a substrate and a diaphragm provided on the substrate. The substrate has a first surface and a second surface opposite the first surface. The substrate has a recess provided in the second surface, a cavity opening to the first surface, and a first through-hole allowing the cavity to communicate with the recess. The diaphragm has a second through-hole formed therein at a position corresponding to the cavity. The second through hole has a diameter smaller than a diameter of the first through-hole.

This device and a method using the device enables only small solid components included in fluid having plural solid components having sizes different from each other to pass without clogging.

DESCRIPTION OF THE PREFERRED EMBODIMENTS

Exemplary Embodiment 1

Figure 1:
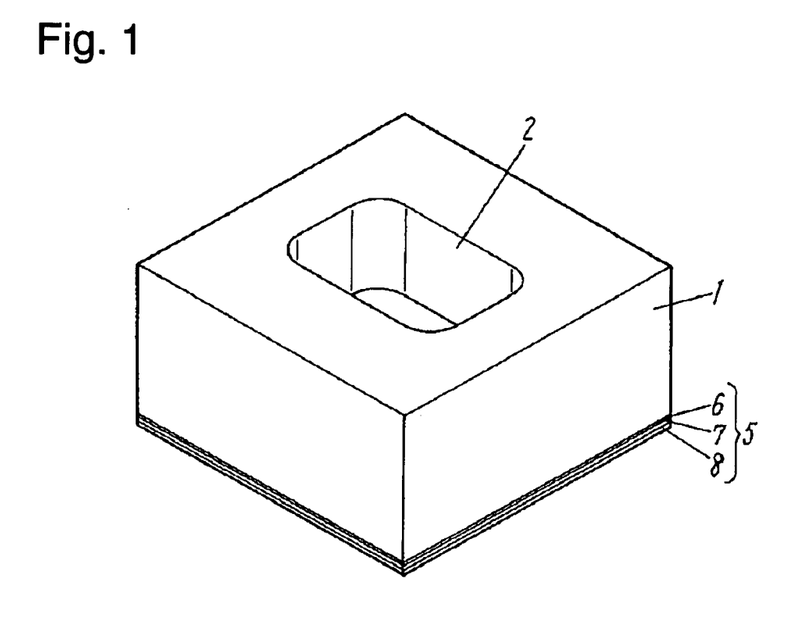
FIG. 1 is a perspective view of a device for separating fine solid components according to Exemplary Embodiment 1 of the present invention.
Figure 2:
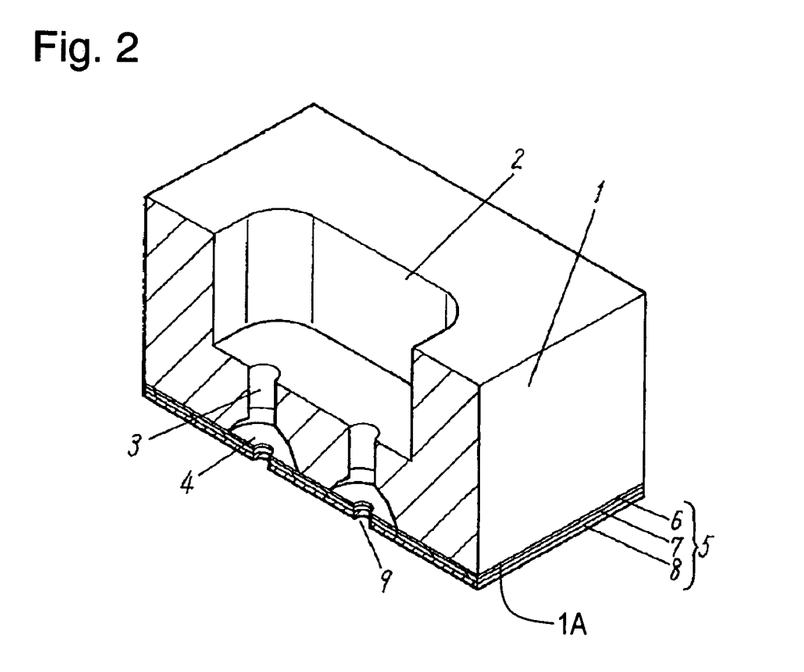
FIG. 2 is a cut-away perspective view of the device according to Embodiment 1.

FIG. 1 is a perspective view of a device for separating fine solid components according to Exemplary Embodiment 1 of the present invention. FIG. 2 is a partially-cut-away perspective view of the device. Substrate 1 made of silicon is hollowed out partially to have recess 2 provided therein. Recess 2 has a bottom having through-hole 3 and cavity 4 which communicates with through-hole 3 and opens to lower surface 1A of substrate 1. Diaphragm 5 is provided on lower surface 1A of substrate 1 and beneath cavity 4. Diaphragm 5 includes conductive layer 6 made of platinum on lower surface 1A of substrate 1, piezoelectric layer 7 made of lead titanate zirconate on conductive layer 6, and conductive layer 8 made of gold on piezoelectric layer 7. A portion of diaphragm 5 corresponding to the center of cavity 4 has through-hole 9 provided therein, and a space in recess 2 of substrate 1 communicates with to the outside of the bottom of substrate 1 via through-hole 3, cavity 4, and through-hole 9. That is, through-hole 3 allows cavity 4 and a bottom of recess 2 to communicate with each other A method for separating various solid components from fluid including the solid compounds with a device according to Embodiment 1 will be described with referring to FIGS. 3 to 9. FIGS. 3 to 9 are sectional views for illustrating an operation of the device.

Figure 3:
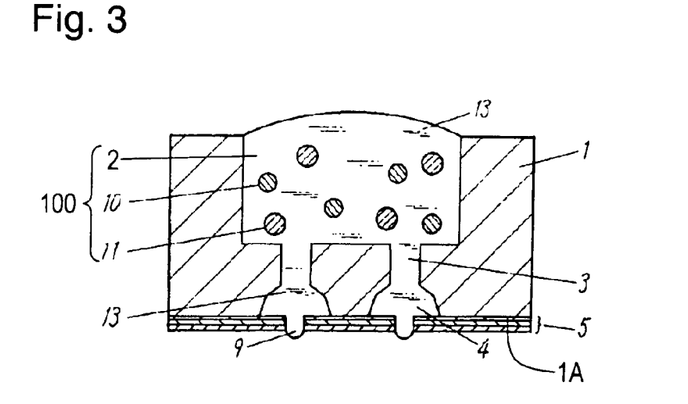
FIG. 3 is a sectional view for illustrating an operation of the device according to Embodiment 1.

First, fluid 100 is put into recess 2 of the device as shown in FIG. 3, and then, fills through-hole 3 and cavity 4. Fluid 100 includes liquid component 13 (e.g. water) and various solid components. The solid components are, for example, two kinds of fine, solid components (e.g. styrene beads) including solid component 10 having a diameter of 5 μm and solid component 11 having a diameter of 6 μm.

The diameter of through-hole 3 is determined to be larger than the diameters of solid components 10 and 11. The diameter of through-hole 9 is determined to be larger than the diameter of solid component 10 and smaller than the diameter of solid component 11.

Figure 4:
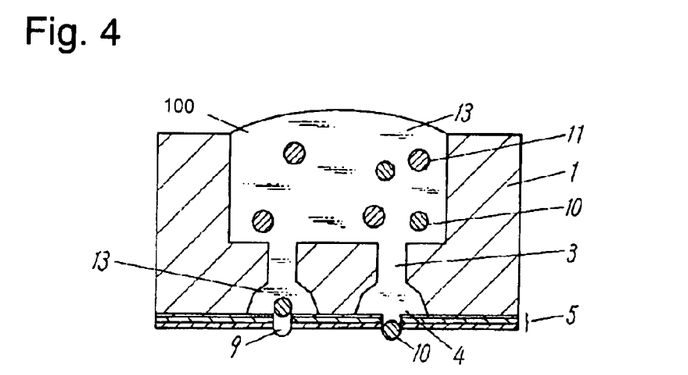
FIG. 4 is a sectional view for illustrating the operation of the device according to Embodiment 1.
Figure 5:
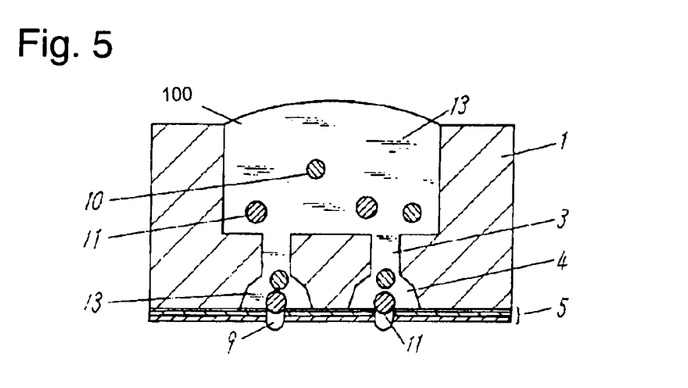
FIG. 5 is a sectional view for illustrating the operation of the device according to Embodiment 1.

Then, a pressure in recess 2 is determined to be higher than a pressure in through-hole 9 by gravity, decompression, or compression. The pressure introduces liquid component 13 and solid components 10 and 11 into cavity 4, as shown in FIG. 4. Then, while solid component 10 having the diameter of 5 μm passes through through-hole 9, solid component 11 having the diameter of 6 μm can not pass through through-hole 9, clogging through-hole 9, as shown in FIG. 5.

Figure 6:
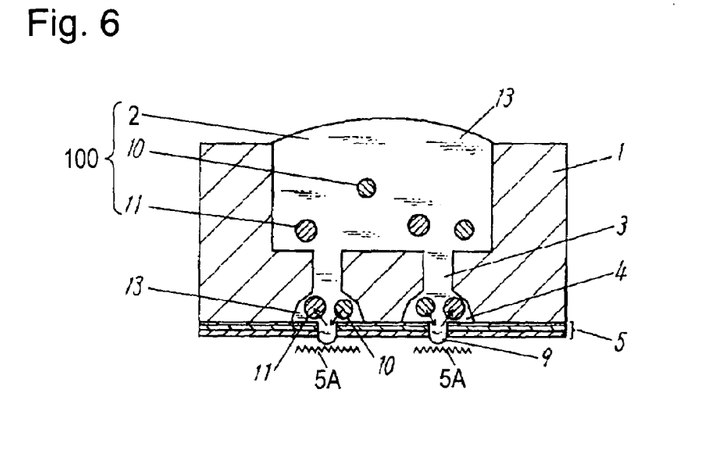
FIG. 6 is a sectional view for illustrating the operation of the device according to Embodiment 1.

When solid component 11 clogs through-hole 9, solid component 10 can not pass through through-hole 9. A voltage is applied between conductive layers 6 and 8 in order to cause piezoelectric layer 7 to vibrate, that is, vibration 5A is applied to diaphragm 5, as shown in FIG. 6. The vibration has solid component 11 depart away from through-hole 9, allowing solid component 10 to pass through the hole again.

Another method of separating solid component 11 from fluid 100 will be described.

Figure 7:
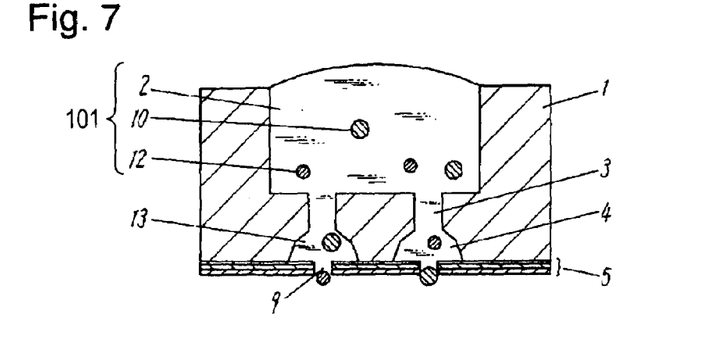
FIG. 7 is a sectional view for illustrating the operation of the device according to Embodiment 1.

As shown in FIG. 7, fluid 101 exists in recess 2. Fluid 101 is mixture of solid component 10 having a diameter of 5 μm and solid component 12 having a diameter of 4 μm) in liquid component 2. The diameter of through-hole 3 is determined to be larger than the diameters of solid components 10 and 12. The diameter of through-hole 9 is determined to be larger than the diameters of solid components 10 and 12. A voltage is applied between conductive layers 6 and 8 in order to cause diaphragm 5 to vibrate, and vibration 5B is propagated to fluid 2 and solid components 10 and 12. Vibration 5B is propagated differently mainly depending on the size of the solid components. Solid components 10 and 12 have respective resonance frequencies according to their sizes. A solid component receiving vibration of a resonance frequency of the component vibrates intensely, hence being prevented from passing through through-hole 9.

Figure 8:
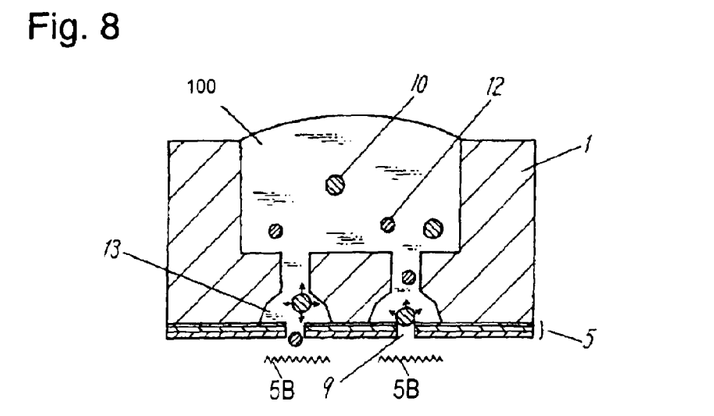
FIG. 8 is a sectional view for illustrating an operation of the device according to Embodiment 1.

Large solid component 10 having the diameter of 5 μm usually passes through through-hole 9 similarly to fine solid component 12 having the diameter of 4 μm. However, as shown in FIG. 8, if vibration 5B of diaphragm 5 has a resonance frequency of solid component 10, solid component 10 vibrates intensely, hence being prevented from passing through through-hole 9. This operation allows only solid component 12 to pass, and hence, fine solid component can be separated. That is, resonant vibration of a predetermined solid component disables only the solid component selectively to pass through through-hole 9.

Vibrations 5A and 5B may be generated by irradiating the bottom of diaphragm 5 with acoustic waves. Namely, air vibrating due to the acoustic waves has diaphragm 5 vibrate.

Figure 9:
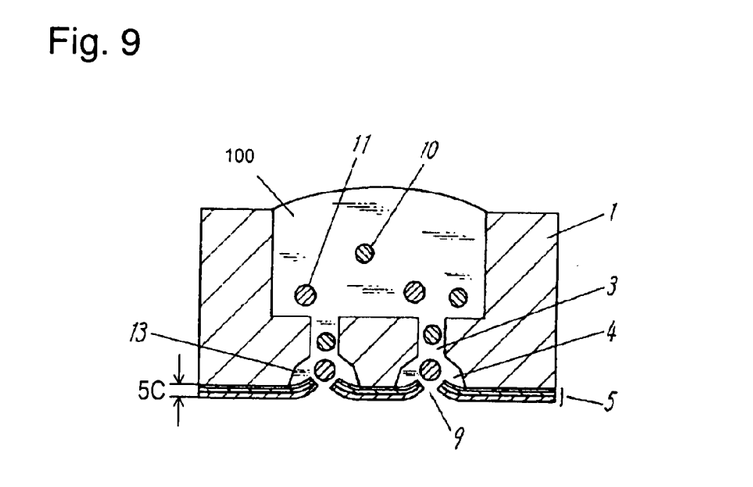
FIG. 9 is a sectional view for illustrating the operation of the device according to Embodiment 1.

Diaphragm 5 has a laminated structure including conductive layer 6, piezoelectric layer 7, and conductive layer 8. A voltage applied between conductive layers 6 and 8 causes distortions in piezoelectric layer 7. An important distortion of the distortions in piezoelectric layer 7 is a distortion of expansion and compression in a direction perpendicular to the direction of an electric field, which is a direction in which conductive layers 6 and 8 face each other. That is, the important distortion is a direction of expansion and compression in a direction parallel to the surface of diaphragm 5. The ratio of the amount of the distortion in this direction to the voltage applied is called piezoelectric constant d31. While the distortion in this direction occurs in piezoelectric layer 7, piezoelectric layer 7 is tightly attached onto conductive layers 6 and 8, thus having diaphragm 5 bend, as shown in FIG. 9. The amount and frequency of the voltage applied to diaphragm 5 determines the amplitude and frequency of vibrations 5A and 5B arbitrarily.

When diaphragm 5 bends, the diameter of through-hole 9 in diaphragm 5 changes according to thickness 5C of diaphragm 5 and the amplitude of the vibration, thereby enabling the size of particles passing through through-hole 9 to be changed. That is, the diameter of through-hole 9 can be changed by adjusting the voltage applied between conductive layers 6 and 8 to change the size of particles passing, hence providing a versatile device for separating fine solid components.

Vibrations 5A and 5B may be generated by irradiating the bottom of diaphragm 5 with acoustic waves. Namely, the air vibrating due to the acoustic waves vibrates diaphragm 5.

A method of manufacturing the device for separating fine solid components according to Embodiment 1 will be described. FIGS. 10 to 15 are sectional views for illustrating processes for manufacturing the device according to Embodiment 1.

Figure 10:
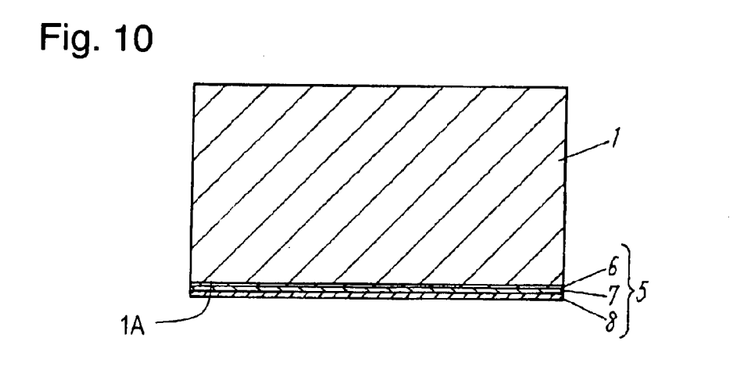
FIG. 10 is a sectional view for illustrating a method of manufacturing the device according to Embodiment 1.

First, as shown in FIG. 10, conductive layer 6 made of platinum is formed on lower surface 1A of substrate 1 made of silicon by sputtering method. Piezoelectric layer 7 made of lead titanate zirconate is formed on conductive layer 6 by sputtering. Conductive layer 8 made of gold is formed on piezoelectric layer 7 by sputtering or vacuum evaporation, thus providing diaphragm 5. Conductive layer 8 may be made of any one of gold, platinum, chrome, titanium, or aluminu; compound or lamination of these instead of gold.

Figure 11:
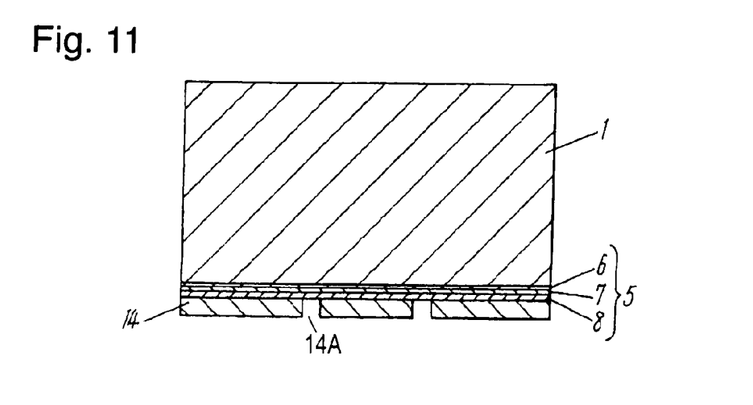
FIG. 11 is a sectional view for illustrating the method of manufacturing the device according to Embodiment 1.

Then, as shown in FIG. 11, resist mask 14 having etching hole 14A is provided on diaphragm 5.

Figure 12:
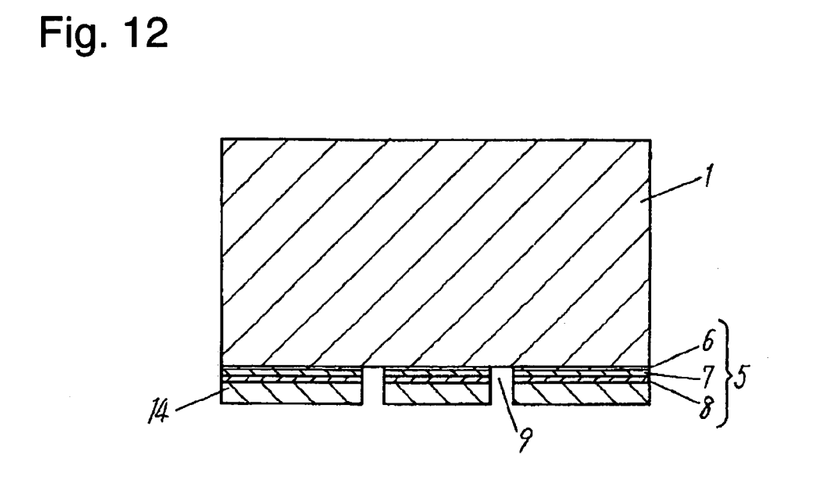
FIG. 12 is a sectional view for illustrating the method of manufacturing the device according to Embodiment 1.

Then, as shown in FIG. 12, diaphragm 5 is etched to reach lower surface 1A of substrate 1 to provide through-hole 9. A dry etching method is preferable to prevent a side wall of through-hole 9 from being etched.

Figure 13:
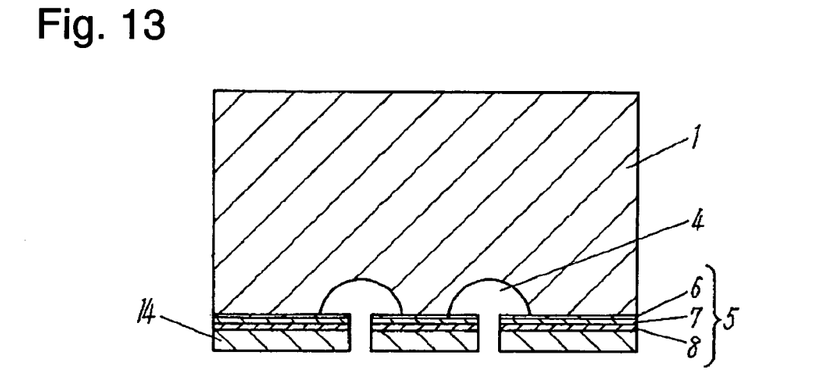
FIG. 13 is a sectional view for illustrating the method of manufacturing the device according to Embodiment 1.

Then, as shown in FIG. 13, cavity 4 is formed in substrate 1 with $XeF_2$ gas facilitating etching of silicon. Substrate 1 made of silicon is etched isotropically by the $XeF_2$ gas, hence having hemispherical cavity 4 therein, as shown in the figure. Cavity 4 may be formed by isotropically-etching similarly with plasma-resolved $SF_6$ gas facilitating the etching.

Figure 14:
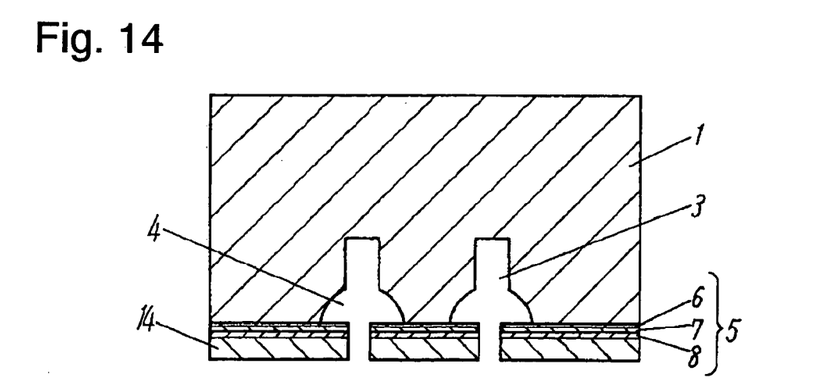
FIG. 14 is a sectional view for illustrating the method of manufacturing the device according to Embodiment 1.

Then, as shown in FIG. 14, substrate 1 is etched from surface 1A with $SF_6$ gas facilitating etching of silicon and $C_4F_8$ gas suppressing the etching. The etching-suppressing gas provides an etched surface of substrate 1 with a protective coating on the surface, hence allowing substrate 1 to be etched only in a direction perpendicular to resist mask 14 and from hole 14A with the etching-facilitating gas. This etching provides substrate 1 with cavity 4 and through-hole 3 therein.

As shown in FIG. 14, through-hole 3 is formed by etching with a mask composed of resist mask 14 and through-hole 9 which are distanced from a bottom of cavity 4, and hence, through-hole 3 has a diameter slightly larger than that of through-hole 9. This relation of the diameters is preferable for allowing a predetermined size of solid components to pass through through-hole 9. That is, through-hole 3 prevents large solid components from flowing in cavity 4, hence preventing through-hole 9 from being clogged.

Resist mask 14 is used to commonly form cavity 4 and through-holes 9 and 3, hence forming cavity 4 and through-holes 9 and 3 and cavity 4 easily by a photolithographic method.

Figure 15:
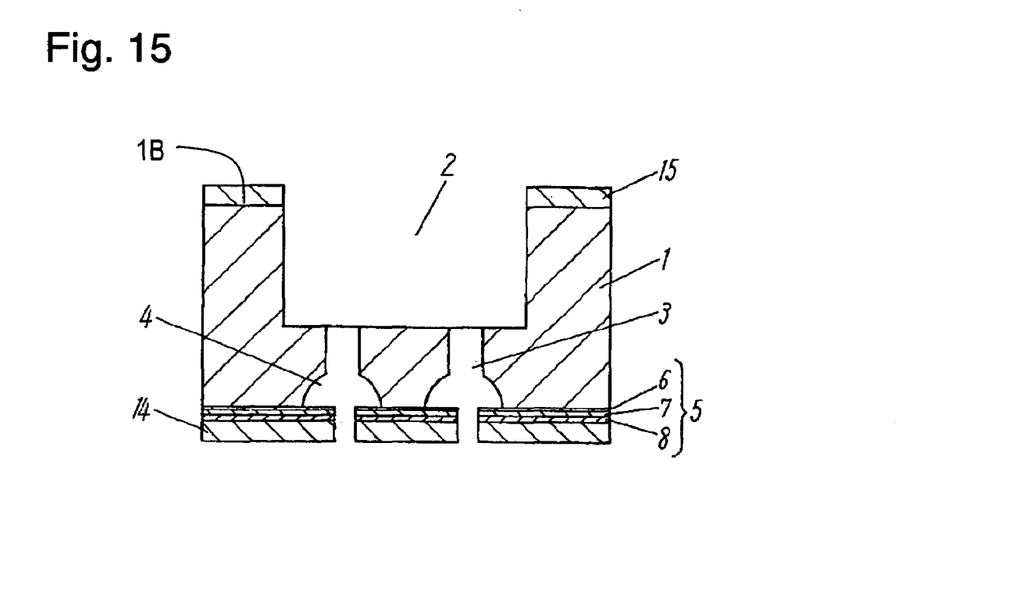
FIG. 15 is a sectional view for illustrating the method of manufacturing the device according to Embodiment 1.

Then, as shown in FIG. 15, resist mask 15 is provided on upper surface 1B of substrate 1, and recess 2 is formed by etching. Finally, resist masks 14 and 15 are removed, and the, substrate 1 and diaphragm 5 are cleaned, thus providing the device for separating fine solid components shown in FIGS. 1 to 9 according to Embodiment 1.

Plural devices can be simultaneously manufactured efficiently by a procedure similarly to that for manufacturing ordinary semiconductor devices. Plural silicon substrates 1 and plural diaphragms 5 corresponding to substrates 1, respectively, are formed all together on a single silicon wafer. Finally, the wafer is divided by dicing into individual substrates 1 with diaphragms 5 corresponding to them, respectively.

Since substrate 1 is made of silicon, platinum composing conductive layers 6, 8 and lead titanate zirconate composing piezoelectric layer 7 can be formed so that they have favorable crystal structures.

Since recess 2, through-holes 3 and 9, and cavity 4 provided in substrate 1 are formed by hewing a silicon wafer, they can be arranged densely, hence providing an extremely small devices. Therefore, unlike a conventional method employing a centrifugal separator, large amounts of samples are not required for separating fine solid components.

Exemplary Embodiment 2

Figure 16:
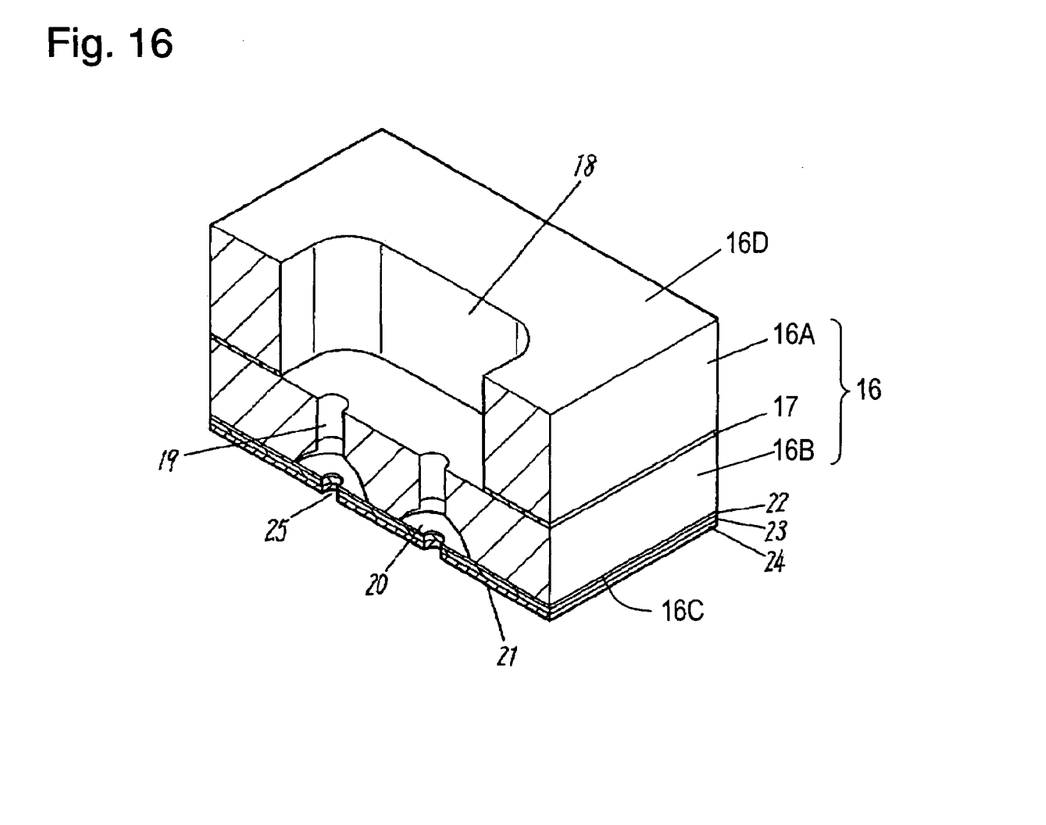
FIG. 16 is a cut-away perspective view of a device for separating fine solid components according to Exemplary Embodiment 2 of the invention.

FIG. 16 is a cut-away perspective view of a device for separating fine solid components according to Exemplary Embodiment 2 of the present invention.

The device according to Embodiment 2 includes substrate 16 having silicon layers 16A and 16B and oxidized film layer 17 between layers 16A and 16B instead of substrate 1 of the device shown in FIGS. 1 to 9 according Embodiment 1. Silicon layer 16B in substrate 16 has lower surface 16C having cavity 20 and through-hole 19 which communicates with cavity 20. Diaphragm 21 is provided on lower surface 16C of substrate 16. Diaphragm 21 has through-hole 25 formed at a position corresponding to the center of cavity 20. Substrate 16 has upper surface 16D having recess 18 formed thereon passing through silicon layer 16A and oxidized film layer 17 and reaching silicon layer 16B.

The device for separating fine solid components according to Embodiment 2 has the same structure and operation as the device shown in FIGS. 1 to 9 according to Embodiment 1, but is manufactured by a method different from that for the device of Embodiment 1

A method of manufacturing the device according to Embodiment 2 will be described. FIGS. 17 to 23 are sectional views for illustrating processes of manufacturing the device according to Embodiment 2.

Figure 17:
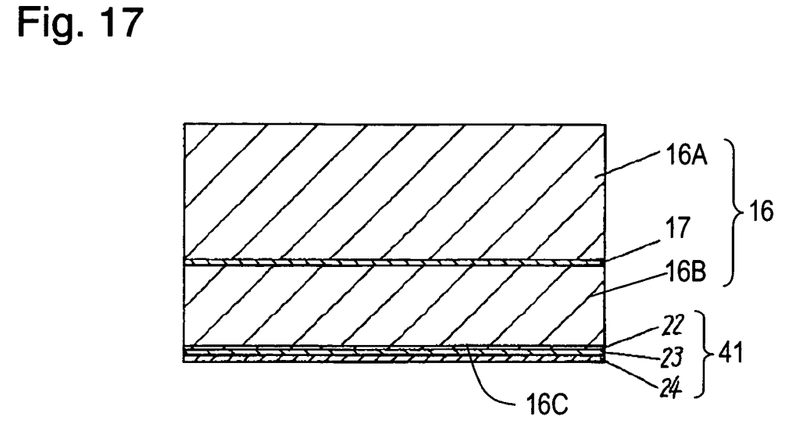
FIG. 17 is a sectional view for illustrating a method of manufacturing the device according to Embodiment 2.

First, as shown in FIG. 17, conductive layer 22 made of platinum is formed by sputtering method on lower surface 16C of substrate 16 including silicon layer 16A, oxidized film layer 17 on silicon layer 16A, and silicon layer 16B. Piezoelectric layer 23 made of lead titanate zirconate is formed on conductive layer 22 by sputtering. Conductive layer 24 made of gold is formed piezoelectric layer 23 by sputtering method or vacuum evaporation method, hence provide diaphragm 41.

Figure 18:
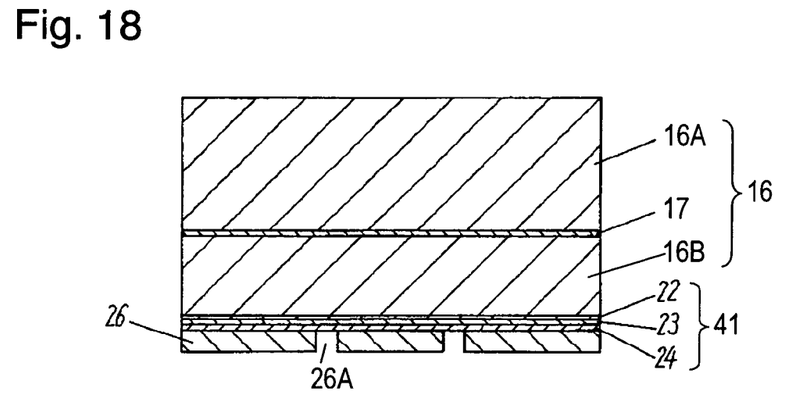
FIG. 18 is a sectional view for illustrating the method of manufacturing the device according to Embodiment 2.

Then, as shown in FIG. 18, resist mask 26 having etching hole 26A is provided on lower surface 24A of diaphragm 41.

Figure 19:
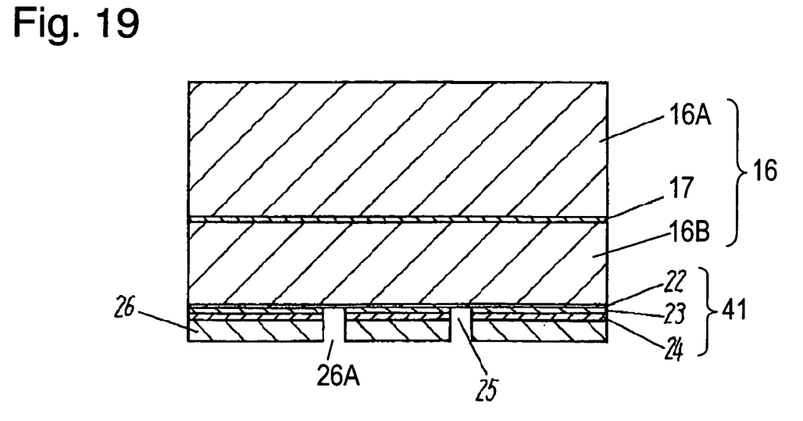
FIG. 19 is a sectional view for illustrating the method of manufacturing the device according to Embodiment 2.

Then, as shown in FIG. 19, diaphragm 41 is etched to form through-hole 25 reaching lower surface 16C of substrate 16. The etching is preferably dry etching to prevent a side of through-hole 25 from being etched.

Figure 20:
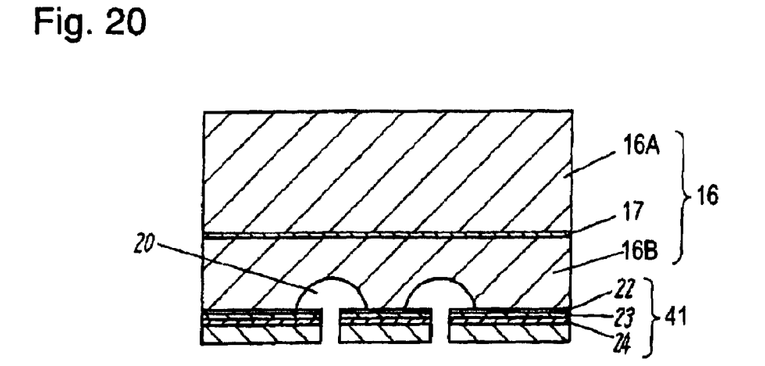
FIG. 20 is a sectional view for illustrating the method of manufacturing the device according to Embodiment 2.

Then, as shown in FIG. 20, $XeF_2$ gas facilitating etching of silicon is introduced through etching hole 26A and through-hole 25 to etch silicon layer 16B to form cavity 20. The etching with the $XeF_2$ gas etched silicon layer 16B isotropically, hence allowing cavity 20 to have a hemispherical shape. Silicon layer 16B can be etched isotropically with plasma-resolved $SF_6$ gas as the etching-facilitating gas to form hemispherical cavity 4 similarly.

Figure 21:
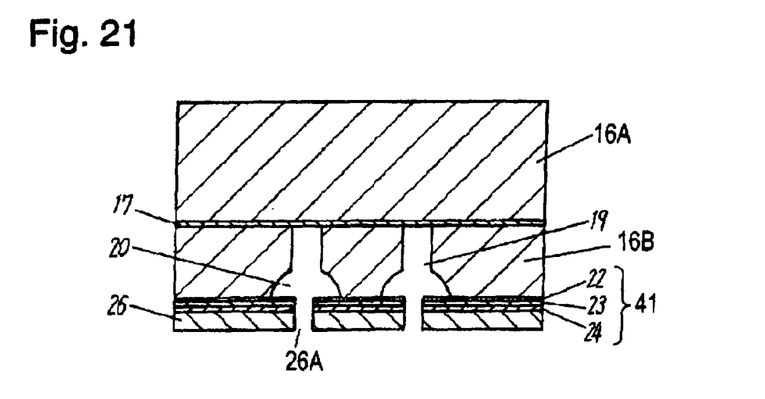
FIG. 21 is a sectional view for illustrating the method of manufacturing the device according to Embodiment 2.

Then, as shown in FIG. 21, silicon layer 16B is etched from lower surface 16C to form through-hole 19 with $SF_6$ gas facilitating etching and $C_4F_8$ gas suppressing etching.

The etching-suppressing gas provides a protective coating on the etched surface of through-hole 16, and the coating allows silicon layer 16B to be etched perpendicularly to resist mask 26 and from resist hole 26A, hence providing silicon layer 16B of substrate 16 with cavity 20 and through-hole 19 therein.

Oxidized film layer 17 of substrate 16 stops the etching of silicon layer 16B substantially completely when through-hole 19 reaches oxidized film layer 17, hence controlling the depth of through-hole 19 easily and accurately.

Figure 22:
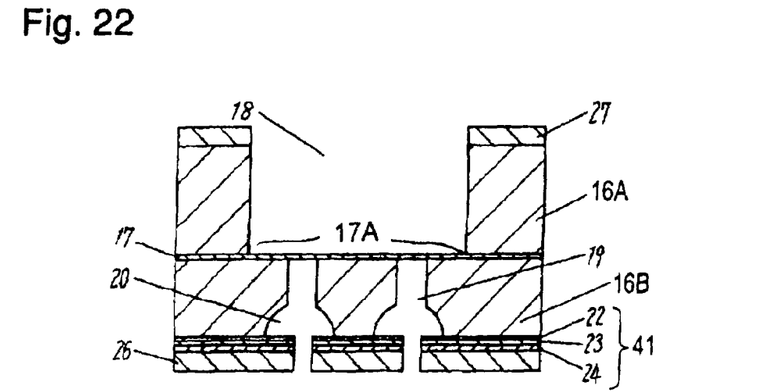
FIG. 22 is a sectional view for illustrating the method of manufacturing the device according to Embodiment 2.

Then, as shown in FIG. 22, resist mask 27 is provided on upper surface 16D of substrate 16, and then, silicon layer 16A of substrate 16 is etched to have recess 18A therein. The etching of silicon layer 16A stops at oxidized film layer 17 substantially completely, hence preventing recess 18A from having an excessively large depth. Further, oxidized film layer 17 still remaining in this stage prevents the etching gas from leaking to through-hole 19, hence avoiding through-hole 19 and cavity 20 to be etched.

Figure 23:
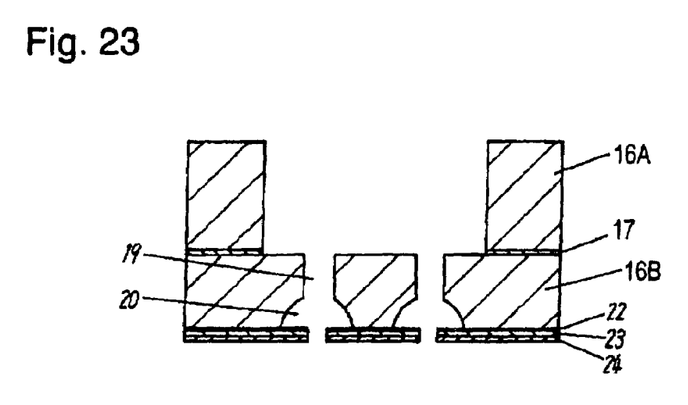
FIG. 23 is a sectional view for illustrating the method of manufacturing the device according to Embodiment 2.

Then, as shown in FIG. 23, portion 17A (FIG. 22) of oxidized film layer 17 is removed by etching, preferably by dry-etching, to provide recess 18, and resist masks 26, 27 are removed. Then substrate 16 and diaphragm 41 are cleaned, thus providing the device is achieved for separating fine solid components according to Embodiment 2.

Plural devices can be simultaneously manufactured efficiently by a procedure similarly to that for manufacturing ordinary semiconductor devices. Plural silicon substrates 16 and plural diaphragms 41 corresponding to substrates 16, respectively, are formed all together on a single silicon wafer. Finally, the wafer is divided by dicing into individual substrates 16 with diaphragms 41 corresponding to them, respectively.

Exemplary Embodiment 3

Figure 24:
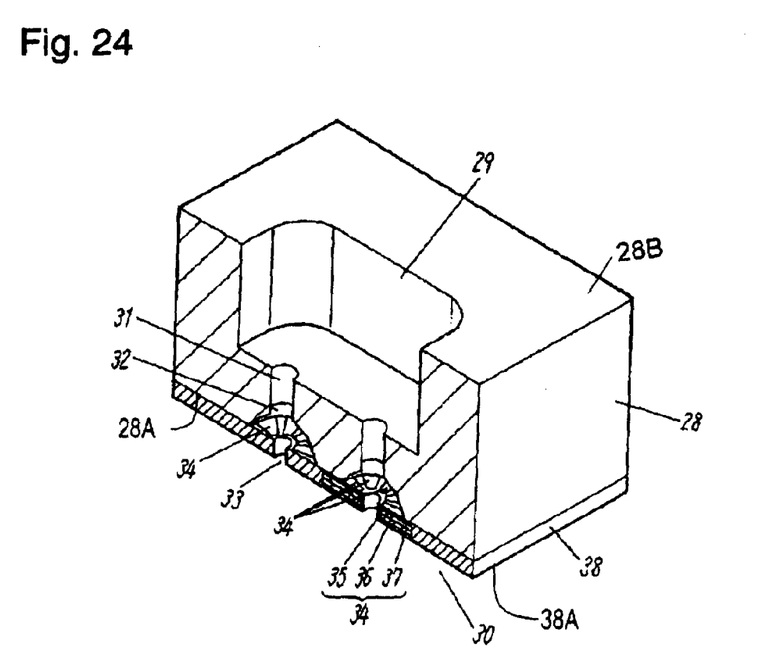
FIG. 24 is a cut-away perspective view of a device for separating fine solid components according to Exemplary Embodiment 3 of the invention.

FIG. 24 is a cut-away perspective view of a device for separating fine solid components according to Exemplary Embodiment 3 of the present invention. This device includes substrate 28 made of silicon and diaphragm 30 on lower surface 28A of substrate 28. Diaphragm 30 includes plural laminated bodies 34 and supporter 38 for supporting laminated bodies 34. Laminated bodies 34 and holding member 38 are arranged on a flat surface. Laminated body 34 includes conductive layer 35 exposed to cavity 32 and located on lower surface 28A of substrate 28, piezoelectric layer 36 on conductive layer 35; and conductive layer 37 on piezoelectric layer 36. Upper surface 28B of substrate 28 is hollowed partially to have recess 29 therein. Substrate 28 has through-hole 31 communicating with the bottom of recess 29, and cavity 32 communicating with through-hole 31 and opening to lower surface 28A. A portion of diaphragm 30 corresponding to the center of cavity 32 has through-hole 33 formed therein. Through-hole 33 extends from lower surface 38A of diaphragm 30 to cavity 32.

Conductive layer 35 of laminated body 34 is made of platinum. Piezoelectric layer 36 is made of lead titanate zirconate. Conductive layer 37 is made of chrome, titanium, gold, platinum, aluminum, or combination of them.

Supporter 38 is made of polyimide, modified acrylate, or silicon resin, and is made preferably of the silicon resin for the device according to Embodiment 3 since the silicon resin deforms largely due to its small Young's modulus.

The device for separating fine solid components according to Embodiment 3 includes diaphragm 30 having plural laminated bodies 34 and supporter 38 for supporting laminated bodies 34, instead of diaphragm 1 of the device according to Embodiment 1 shown in FIGS. 1 to 9. The device according to Embodiment 2 shown in FIG. 16 may includes diaphragm 38 shown in FIG. 24 instead of diaphragm 41.

An operation for separating fine solid components is the same as the device according to Embodiment 1 and is not described.

In the device according to Embodiment 3, supporter 38 made of resin material allows each laminated body 34 to deform intensely due to a voltage applied between conductive layers 35 and 37, thus not preventing the deforming. This structure makes a change of the diameter of through-hole 33 larger than that of through-holes 9 and 25 of the devices according to embodiments 1 and 2. Namely, the diameter of through-hole 33 can be changed, hence providing a versatile device capable of controlling a wide range of diameters of fine solid components.

What is claimed:

1. A device for separating a fine solid component, said device comprising:

a substrate having a first surface and a second surface opposite the first surface, the substrate having a recess, a cavity, and a first through-hole, the recess being provided in the second surface, the recess having a bottom, the cavity opening to the first surface, the first through-hole allowing the cavity to communicate with the bottom of the recess; and a diaphragm on the first surface of the substrate, the diaphragm having a second through-hole therein at a position corresponding to the cavity, the second through-hole having a diameter smaller than a diameter of the first through-hole, wherein the diaphragm includes a first conductive layer on the first surface of the substrate, a piezoelectric layer on the first conductive layer, and a second conductive layer on the piezoelectric layer.

2. The device as defined in claim 1, wherein the first conductive layer includes platinum, wherein the piezoelectric layer includes lead titanate zirconate, and wherein the second conductive layer includes at least one of gold, platinum, chrome, titanium, and aluminum.

3. The device as defined in claim 1, wherein the substrate is made of silicon.

4. The device as defined in claim 1, wherein the cavity has a hemispherical shape opening to the first surface of the substrate.

5. The device as defined in claim 1, wherein the substrate includes a first silicon layer, an oxidized film layer on the first silicon layer, and a second silicon layer on the oxidized film layer, wherein the recess is formed in the first silicon layer and the oxidized film layer, and wherein the first through-hole is formed in the second silicon layer.

6. A device for separating a fine solid component, said device comprising:

a substrate having a first surface and a second surface opposite the first surface, the substrate having a recess, a cavity, and a first through-hole, the recess being provided in the second surface, the recess having a bottom, the cavity opening to the first surface, the first through-hole allowing the cavity to communicate with the bottom of the recess; and a diaphragm on the first surface of the substrate, the diaphragm having a second through-hole therein at a position corresponding to the cavity, the second through-hole having a diameter smaller than a diameter of the first through-hole,
wherein the diaphragm includes
a laminated body including
 a first conductive layer exposed to the cavity of the substrate,
 a piezoelectric layer on the first conductive layer, and
 a second conductive layer on the piezoelectric layer, and
a supporter for supporting the laminated body.

7. The device as defined in claim 6,
wherein the first conductive layer includes platinum,
wherein the piezoelectric layer includes lead titanate zirconate, and
wherein the second conductive layer includes at least one of gold, platinum, chrome, titanium, and aluminum.

8. The device of claim 6, wherein the substrate is made of silicon.

9. The device of claim 6, wherein the cavity has a hemispherical shape opening to the first surface of the substrate.

10. The device of claim 6, wherein the substrate includes a first silicon layer, an oxidized film layer on the first silicon layer, and a second silicon layer on the oxidized film layer,
wherein the recess is formed in the first silicon layer and the oxidized film layer, and
wherein the first through-hole is formed in the second silicon layer.

11. A device for separating a fine solid component, said device comprising:
a substrate having a first surface and a second surface opposite the first surface, the substrate having a recess, a cavity, and a first through-hole, the recess being provided in the second surface, the recess having a bottom, the cavity opening to the first surface, the first through-hole allowing the cavity to communicate with the bottom of the recess; and
a diaphragm on the first surface of the substrate, the diaphragm having a second through-hole therein at a position corresponding to the cavity, the second through-hole having a diameter smaller than a diameter of the first through-hole,
wherein the diaphragm includes
a plurality of laminated bodies each including
 a first conductive layer exposed to the cavity of the substrate,
 a piezoelectric layer on the first conductive layer, and
 a second conductive layer on the piezoelectric layer, and
a supporter for supporting the laminated body.

12. The device as defined in claim 11,
wherein the first conductive layer includes platinum,
wherein the piezoelectric layer includes lead titanate zirconate; and
wherein the second conductive layer includes at least one of gold, platinum, chrome, titanium, and aluminum.

13. The device of claim 11, wherein the substrate is made of silicon.

14. The device of claim 11, wherein the cavity has a hemispherical shape opening to the first surface of the substrate.

15. The device of claim 11, wherein the substrate includes a first silicon layer, an oxidized film layer on the first silicon layer, and a second silicon layer on the oxidized film layer,
wherein the recess is formed in the first silicon layer and the oxidized film layer, and
wherein the first through-hole is formed in the second silicon layer.

16. A method of separating a first solid component and a second solid component from fluid including the first solid component, the second solid component, and liquid component, said method comprising:
preparing a device comprising:
 a substrate having a first surface and a second surface opposite the first surface, the substrate having a recess having a bottom that is the second surface, a cavity opening to the first surface, and a first through-hole for allowing the cavity to communicate with the bottom of the recess, and
 a diaphragm on the first surface of the substrate, the diaphragm having a second through-hole at a position corresponding to the cavity, the second through-hole having a diameter smaller than a diameter of the first through-hole;
filling the first through-hole and the cavity with such a fluid by putting the fluid into the recess of the substrate;
allowing the diaphragm to vibrate; and
taking out the first solid component from the cavity of the substrate through the second through-hole.

17. The method as defined in claim 16,
wherein the diaphragm includes a first conductive layer on the first surface of the substrate, a piezoelectric layer on the first conductive layer, and a second conductive layer on the piezoelectric layer, and
wherein said allowing of the diaphragm to vibrate comprises bending the diaphragm by applying a voltage between the first conductive layer and the second conductive layer.

18. The method as defined in claim 16, wherein said allowing of the diaphragm to vibrate comprises allowing the diaphragm to vibrate at a resonance frequency of the second solid component.

* * * * *